(12) United States Patent
Delbrassinne et al.

(10) Patent No.: US 10,005,110 B2
(45) Date of Patent: Jun. 26, 2018

(54) FOAM CONTROL COMPOSITION

(75) Inventors: Pascal Delbrassinne, Rixensart (BE);
Laurence Gallez, Jurbise (BE);
Mathilde Guette, Saint Benoit (FR);
Jean-Paul Lecomte, Brussels (BE)

(73) Assignee: DOW SILICONES CORPORATION, Midland, MI (US)

( * ) Notice: Subject to any disclaimer, the term of this patent is extended or adjusted under 35 U.S.C. 154(b) by 0 days. days.

(21) Appl. No.: 13/985,310

(22) PCT Filed: Feb. 16, 2012

(86) PCT No.: PCT/US2012/025474
§ 371 (c)(1),
(2), (4) Date: Aug. 14, 2013

(87) PCT Pub. No.: WO2012/134651
PCT Pub. Date: Oct. 4, 2014

(65) Prior Publication Data
US 2013/0327364 A1    Dec. 12, 2013

(30) Foreign Application Priority Data

Feb. 16, 2011  (GB) .................................. 1102750.5

(51) Int. Cl.
| | | |
|---|---|---|
| *B08B 3/00* | (2006.01) | |
| *B08B 7/00* | (2006.01) | |
| *C11D 3/04* | (2006.01) | |
| *C11D 3/12* | (2006.01) | |
| *C11D 3/37* | (2006.01) | |
| *C11D 11/00* | (2006.01) | |
| *B08B 3/04* | (2006.01) | |
| *C11D 3/00* | (2006.01) | |

(52) U.S. Cl.
CPC .............. *B08B 3/04* (2013.01); *C11D 3/0026* (2013.01); *C11D 3/1246* (2013.01); *C11D 3/373* (2013.01); *C11D 3/3707* (2013.01); *C11D 3/3749* (2013.01); *C11D 11/0017* (2013.01)

(58) Field of Classification Search
None
See application file for complete search history.

(56) References Cited

U.S. PATENT DOCUMENTS

| | | | |
|---|---|---|---|
| 3,959,175 A | 5/1976 | Smith, Jr. et al. | |
| 4,894,177 A | 1/1990 | Starch | |
| 4,978,471 A * | 12/1990 | Starch .......................... | 516/119 |
| 5,045,225 A | 9/1991 | Aronson et al. | |
| 5,229,033 A | 7/1993 | Nguyen et al. | |
| 5,562,862 A | 10/1996 | Berzansky, Jr. et al. | |
| 5,681,808 A | 10/1997 | Kobayashi et al. | |
| 5,777,059 A | 7/1998 | Datz-Siegel et al. | |
| 6,124,490 A | 9/2000 | Gormley et al. | |
| 6,165,968 A | 12/2000 | Lenoble | |
| 6,180,712 B1 | 1/2001 | Ishikawa et al. | |
| 6,369,021 B1 | 4/2002 | Man et al. | |
| 6,404,064 B1 | 6/2002 | Tsai et al. | |
| 6,512,015 B1 | 1/2003 | Elms et al. | |
| 6,521,586 B1 * | 2/2003 | Hoogland .......... | B01D 19/0404 510/347 |
| 6,521,587 B1 | 2/2003 | L'Hostis et al. | |
| 6,656,975 B1 | 12/2003 | Christiano et al. | |
| 7,407,991 B2 | 8/2008 | Creutz et al. | |
| 7,550,514 B2 | 6/2009 | Rautschek et al. | |
| 7,619,043 B2 | 11/2009 | Rautschek et al. | |
| 7,632,890 B2 | 12/2009 | Creutz et al. | |
| 8,084,566 B2 | 12/2011 | Rautschek et al. | |
| 8,138,294 B2 | 3/2012 | Henning et al. | |
| 8,222,303 B2 | 7/2012 | Herzig et al. | |
| 8,536,109 B2 | 9/2013 | Delbrassinne et al. | |
| 8,633,147 B2 | 1/2014 | Paul et al. | |
| 8,653,214 B2 | 2/2014 | Venzmer et al. | |
| 8,673,985 B2 | 3/2014 | Lange et al. | |
| 8,785,587 B2 | 7/2014 | Wagner et al. | |
| 9,175,141 B2 | 11/2015 | Wray et al. | |
| 9,487,736 B2 | 11/2016 | Gallez et al. | |
| 2001/0009896 A1 | 7/2001 | Hoogland et al. | |
| 2002/0155978 A1 | 10/2002 | Man et al. | |
| 2002/0170323 A1 * | 11/2002 | Stahl ...................... | D06F 15/00 68/122 |
| 2003/0056301 A1 | 3/2003 | Dekker et al. | |
| 2003/0166494 A1 | 9/2003 | Man et al. | |
| 2004/0077516 A1 | 4/2004 | Man et al. | |
| 2007/0161539 A1 | 7/2007 | Hernandez | |
| 2007/0167346 A1 | 7/2007 | Creutz et al. | |
| 2008/0021152 A1 | 1/2008 | Rautschek et al. | |
| 2008/0021182 A1 | 1/2008 | Jones | |
| 2008/0293606 A1 | 11/2008 | Rautschek et al. | |
| 2009/0069522 A1 | 3/2009 | Hessefort et al. | |

(Continued)

FOREIGN PATENT DOCUMENTS

| | | |
|---|---|---|
| CN | 1284546 A | 2/2001 |
| CN | 1478141 A | 2/2004 |

(Continued)

OTHER PUBLICATIONS

Farn, Richard J. Chemistry and Technology of Surfactants: 2006. Google Books. Accessed Jun. 2015.*

(Continued)

*Primary Examiner* — Eric W Golightly
*Assistant Examiner* — Arlyn I Rivera-Cordero
(74) *Attorney, Agent, or Firm* — Warner Norcross & Judd LLP

(57) ABSTRACT

A process for washing a substrate. The process involves providing a detergent composition that includes a surfactant and an antifoam. The antifoam comprises a hydrophobic fluid having a surface tension of at least 27 mN/m and less than 40 mN/m and a finely divided solid hydrophobic filler dispersed in the hydrophobic fluid. The process further involves washing the substrate in an aqueous medium with the detergent composition. The antifoam does not affect foaming during the washing step. During the washing step, the detergent composition is applied to the substrate. The process further involves rinsing the substrate with the applied detergent composition with water, whereby foaming during the rinsing step is inhibited.

20 Claims, No Drawings

(56) References Cited

U.S. PATENT DOCUMENTS

| | | | |
|---|---|---|---|
| 2010/0093598 | A1 | 4/2010 | Davio et al. |
| 2010/0233104 | A1 | 9/2010 | Drake et al. |
| 2011/0056249 | A1 | 3/2011 | Cho et al. |
| 2012/0329701 | A1 | 12/2012 | Paul |
| 2013/0309498 | A1 | 11/2013 | Chao et al. |
| 2013/0327364 | A1 | 12/2013 | Delbrassinne et al. |
| 2015/0038388 | A1 | 2/2015 | Gallez et al. |
| 2016/0184214 | A1 | 6/2016 | Bernet et al. |

FOREIGN PATENT DOCUMENTS

| | | |
|---|---|---|
| DE | 102006044839 | 4/2008 |
| EP | 0210731 | 2/1987 |
| EP | 0496510 | 7/1992 |
| EP | 0685250 A1 | 12/1995 |
| EP | 0811584 A1 | 12/1997 |
| EP | 1075863 A2 | 2/2001 |
| EP | 1075864 | 2/2001 |
| JP | 08192001 A | 7/1996 |
| JP | H09137190 A | 5/1997 |
| JP | 2002053440 | 2/2002 |
| JP | 2007211205 A | 8/2007 |
| JP | 2008024760 A | 2/2008 |
| JP | 5282353 | 9/2013 |
| WO | WO9100763 | 1/1991 |
| WO | WO1999032539 | 7/1999 |
| WO | WO 02/44312 A2 | 6/2002 |
| WO | WO 0244312 A2 | 6/2002 |
| WO | WO2004047779 | 6/2004 |
| WO | WO2005058454 A1 | 6/2005 |
| WO | WO2005058455 A1 | 6/2005 |
| WO | WO2006063483 | 6/2006 |
| WO | WO2008145423 A1 | 12/2008 |
| WO | WO 2008152042 A1 | 12/2008 |
| WO | WO2012134651 | 10/2012 |
| WO | WO 2013/122619 A1 | 8/2013 |
| WO | WO2013122619 A1 | 8/2013 |
| WO | WO2015018853 A1 | 2/2015 |

OTHER PUBLICATIONS

Wu, Wen-Zhong. Environmental Behavior and Ecotoxicological Impact of Persistent Organic Pollutants (POP) in Wildlife, with Special Emphasis on the Aquatic Ecosystem. Germany, 1999. Google books. Web. Apr. 2016. https://books.google.com/books?id=JjERXWPuy90C&pg=PA92&lpg=PA92&dq=linear+alkylbenzene+sulfonate+(las)+critical+micelle&source=bl&ots=UoMz.*

"Solid Surface Energy Data (SFE) for Common Polymers", http://www.surface-tension.de/solid-surface-energy.htm, last updated Nov. 20, 2007, printed Mar. 21, 2014, 2 pages.

Surface Energy Data for PDMS: Polydimethylsiloxane, CAS #9016-00-6, Diversified Enterprises, 2009, 1 page.

Kuo, Dr. Alex C.M., Dow Corning Corporation, "Silicone Release Coatings for the Pressure Sensitive Industry—Overview and Trends; Part I—An Introduction to Silicone", May 2004, pp. 1-4.

Woodward, Roger P., Ph.D., First Ten Angstroms, "Surface Tension Measurements Using the Drop Shape Method", Mar. 1995, pp. 1-6.

English language abstract for CN 1284546; original document extracted from espacenet.com database on Jun. 18, 2014, 1 page.

English language abstract for CN 1478141; original document extracted from espacenet.com database on Jun. 18, 2014, 1 page.

Woodward, Roger P., "Surface Tension Measurements Using the Drop Shape Method," First Ten Angstroms, 465 Dinwiddie Street, Portsmouth, VA 23704, pp. 1-6, dated Mar. 1995.

International Search Report for Application PCT/US2012/025474 dated Jun. 1, 2012, 4 pages.

Schwartz, et al, "Surface-Active Agents and Detergents," vols. I and II, dated Dec. 11, 2007.

Wu, Wen-Zhong. Environmental Behavior and Ecotoxicological Impact of Persistent Organic Pollutants (POP) in Wildlife, with Special Emphasis on the Aquatic Ecosystem. Germany, 1999. Google Books. Web. Apr. 2016.

English language abstract and machine assisted English translation for JP08192001 extracted from http://www4.ipdl.inpit.go.jp/ database, 49 pages, Publication Date: Jul. 30, 1996.

English language abstract and machine assisted English translation for JP2002053440 extracted from http://www4.ipdl.inpit.go.jp/ database, 43 pages, Publication Date: Feb. 19, 2002.

English language abstract for DE102006044839 extracted from http://www.worldwide.espacenet.com database on Jan. 11, 2016, 1 page, Publication Date: Apr. 3, 2008.

English language abstract and machine assisted English translation for WO2008145423 extracted from http://www.worldwide.espacenet.com database,13 pages, Publication Date: Dec. 4, 2008.

International Search Report, PCT/US2012/050977, dated Nov. 16, 2012, 3 pages.

International Search Report, PCT/EP2014/066875, dated Nov. 21, 2014, 4 pages.

English language abstract and machine assisted English translation for JPH09137190A extracted from http://www.worldwide.espacenet.com database, 23 pages, Date: May 27, 1997.

English language abstract and machine assisted English translation for JP2007211205A extracted from http://www.worldwide.espacenet.com database, 17 pages, Date: Aug. 23, 2007.

English language abstract and machine assisted English translation for JP2008024760A extracted from http://www.worldwide.espacenet.com database, 25 pages, Date: Feb. 7, 2008.

Nippon Polybutene Business Solutions, JX Energy, Oct. 23, 2015, URL, http://www.noe.jx-group.co.jp/business/chemical/e71_buch_016.html, 8 pages.

Report on Patentability for PCT/US2012/050977, dated Aug. 19, 2014, 7 pages.

Written Opinion for PCT/US2012/050977, dated Aug. 19, 2014, 6 pages.

* cited by examiner

FOAM CONTROL COMPOSITION

RELATED APPLICATIONS

This application is the National Stage of International Patent Application No. PCT/US2012/025474, filed on Feb. 16, 2012, which claims priority to and all the advantages of Great Britain Application No. GB 1102750.5, filed on Feb. 16, 2011, the content of which is incorporated herein by reference.

FIELD OF THE INVENTION

This invention relates to foam control agents for use in laundry detergents and to detergent compositions containing the foam control agents. The foam control agents of the invention can be added to detergent compositions to inhibit unwanted foaming when the detergent is used in washing.

BACKGROUND OF THE INVENTION

Washing of clothes by hand or in semi-automatic machines is widespread in many countries; seventy percent of the world's population still wash their clothes in this way. When doing so, consumers usually like to see a lot of lather (foam) as they associate foaming with detergent efficiency. However, removing the lather requires numerous rinses, generally three or more rinses, which costs a lot of effort and wastes water.

Most foam control agents are designed for use in automatic washing machines. They are active in the washing stage to avoid overflow of foam. They are less suitable for hand washing applications as they eliminate or greatly reduce the lather in the washing stage. A foam control agent that would not greatly reduce the foam level in the washing stage but would cause fast defoaming in the rinse would allow saving of significant quantities of water and reduce the time and efforts needed for rinsing.

According to the present inventive concepts, a new antifoam has been devised which is active in diluted surfactant concentration and which is inactive in concentrated surfactant solution. It will be appreciated that the main difference between the washing stage and the rinse stage of a wash process is the surfactant concentration.

SUMMARY OF THE INVENTION

This invention relates to a process for washing a substrate. The process involves providing a detergent composition that includes a surfactant and an antifoam. The antifoam comprises (a) a hydrophobic fluid having a surface tension of at least 27 mN/m and less than 40 mN/m, and (b) a finely divided solid hydrophobic filler dispersed in the hydrophobic fluid. The process further involves washing the substrate in an aqueous medium with the detergent composition. The antifoam does not affect foaming during the washing step. During the washing step, the detergent composition is applied to the substrate. The process further involves rinsing the substrate with the applied detergent composition with water, whereby foaming during the rinsing step is inhibited. The concentration of the surfactant in the aqueous medium during the washing step is above a critical micelle concentration and the concentration of the surfactant in the rinse water from the rinsing step is below the critical micelle concentration. The substrate may be fabric and the detergent composition may be a laundry detergent composition. The hydrophobic fluid may be an organopolysiloxane fluid or polyisobutylene. The finely divided solid hydrophobic filler may be hydrophobic silica. The laundry detergent composition may be in powder form and may contain a granulated foam control agent comprising the antifoam supported on a particulate carrier.

Additional aspects of the invention will be apparent to those of ordinary skill in the art in view of the detailed description of various embodiments, a brief description of which is provided below.

DETAILED DESCRIPTION

A detergent composition according to the inventive concepts comprises a detersive surfactant and an antifoam comprising (a) a hydrophobic fluid and (b) a finely divided solid hydrophobic filler dispersed in the hydrophobic fluid. The hydrophobic fluid (a) has a surface tension which is greater than or approximately equal to the dynamic surface tension of an aqueous dispersion of the detergent at above the critical micelle concentration of the surfactant but is less than 62. By 'greater than or approximately equal to the dynamic surface tension of an aqueous dispersion of the detergent at above the critical micelle concentration', it is intended that the static surface tension of the hydrophobic fluid is at least 95% of the dynamic surface tension of an aqueous dispersion of the detergent at above the critical micelle concentration.

In some embodiments, the hydrophobic fluid has a surface tension of at least 27 mN/m and less than 40 mN/m. The hydrophobic fluid having a surface tension between 27 and 40 mN/m does not contain any polar groups having active hydrogen that can be ionized in the aqueous medium with the detergent composition. Such groups are, for example, carboxylic, sulfonate, sulfate, amide or phosphate.

The dynamic surface tension of an aqueous dispersion of the detergent is measured on a 0.35% by weight aqueous solution of the detergent by the method of ASTM D-3825 using a Sita DynoTester bubble pressure tensiometer supplied by Sita Messtechnik GmbH. A bubble formed within a liquid is being compressed by the surface tension. The resulting pressure rises with the decreasing bubble radius. This increased pressure, in comparison to the outside of the bubble, is used to measure surface tension. In the test, air is pumped through a capillary into a liquid. The so-created bubble surface bulges, hence continuously decreasing the bubble radius. During this process, the pressure rises to a maximum pressure. Here, the bubble has its smallest radius. This radius equals the radius of the capillary and forms a half sphere. After passing this point, the bubble bursts and breaks away from the capillary. Now, a new bubble can form at the capillary. During this process, the characteristic course of pressure can be measured in the bubble. From this characteristic course of pressure, the surface tension can be calculated. The bubble pressure tensiometer produces bubbles with increasing lifetime, starting at 0.030 seconds and increasing by a factor of 1.3 up to 40 seconds. The dynamic surface tension specified herein is the value taken at the end of the measurement, which corresponds to a bubble lifetime of 40 seconds. This is a dynamic measurement, which is quite representative of the use of the surfactant in the washing and rinsing process.

The surface tension of the hydrophobic fluid (a) is measured by the drop shape method. In this test, a drop of pure antifoam compound is made in air by using a syringe and the surface tension is calculated from measurements of the pendant drop curvature. The drop shape test method is explained in the paper 'Surface tension measurements using the drop shape method' by R. P. Woodward published by First Ten Angstroms of 465 Dinwiddie Street, Portsmouth, Va., U.S.A. The surface tension of the antifoam measured by the drop shape method may be regarded as the static surface tension. This is less representative of the use of the antifoam in the washing and rinsing process, but any attempt to measure the dynamic surface tension of the antifoam alone will also be unrepresentative of the use of the antifoam in the washing and rinsing process. All surface tension measurements specified herein (both dynamic surface tension measurements and static surface tension measurements) are surface tensions at 25° C.

It is believed that an antifoam compound which has a much lower surface tension than the dynamic surface tension of the detergent solution will migrate quickly to the bubble interface and break the foam, as demonstrated in the wash by conventional antifoams used in laundry detergents. According the inventive concepts described herein, the foam inhibitor, which is based on a hydrophobic fluid having a surface tension greater than the surface tension of conventional antifoams used in laundry detergents, does not spread on the surface of concentrated surfactant solution and is ineffective to reduce foam in the washing stage when surfactant concentration is high. It is believed that an antifoam compound which has a surface tension greater than or approximately equal to the dynamic surface tension of the aqueous dispersion of the detergent in the wash, where the surfactant solution is above the critical micelle concentration, will migrate too slowly to the bubble interface and will hardly break the foam.

Once the detergent solution is diluted below the critical micelle concentration of the surfactant, the surface tension of the solution increases and becomes higher than the antifoam surface tension. Migration of the surfactant to the bubble interface becomes less effective below the critical micelle concentration. This happens in the rinse cycle. Surprisingly, it was been observed that despite dilution of the antifoam by removal of washing liquor and replacement with fresh water in each rinsing step, the antifoam of the inventive concepts is still effective at the rinsing stage. Migration of antifoam to the bubble interface competes effectively with migration of the surfactant, and the antifoam starts to be effective.

A process according to the inventive concepts for inhibiting foam during the washing of a substrate comprises (i) applying a detergent to a substrate in an aqueous medium and (ii) rinsing the substrate from step (i), wherein the detergent in step (i) contains an antifoam comprising (a) a hydrophobic fluid having a surface tension of at least 27 mN/m and less than 40 mN/m, and (b) a finely divided solid hydrophobic filler dispersed in the hydrophobic fluid The invention includes a fabric washing process comprising washing a fabric in an aqueous dispersion of a detergent composition according to the invention as defined above at a concentration of surfactant in the aqueous dispersion above the critical micelle concentration, and subsequently rinsing the fabric in water wherein the concentration of surfactant is below the critical micelle concentration.

The critical micelle concentration of a surfactant in aqueous dispersion can be found by measuring the dynamic surface tension of aqueous dispersions of that surfactant at varying concentrations. Surfactant molecules absorb at the air/water interface, reducing surface tension. As the interface becomes saturated at the critical micelle concentration, the surfactant molecules start to form micelles, with the surface tension remaining constant. A graph of surface tension against surfactant concentration shows an abrupt change of gradient around the critical micelle concentration. Above the critical micelle concentration, the surface tension is substantially constant over a range of surfactant concentrations. Below the critical micelle concentration, the surface tension increases with increasing dilution, until it approaches the surface tension of water for very dilute dispersions. The critical micelle concentration for most surfactants commonly used in laundry detergent powders is equivalent to between 0.2 g/L and 0.6 g/L detergent powder, compared to the recommendations of the suppliers on the detergent packages for a concentration of powder detergent in the wash of 2 to 4 g/L. The surface tension of an aqueous dispersion of a laundry detergent at above the critical micelle concentration is usually in the range 25 to 30 mN/m. For a typical powder detergent used at 3.5 g/L with a sevenfold dilution in each rinsing step, it has been observed that the surface tension in the wash is 27 mN/m, the surface tension in the first rinse is 35 mN/m and the surface tension in the second rinse is 62 mN/m.

The hydrophobic fluid (a) used as the antifoam can, for example, be a fluid organopolysiloxane. Fluid organopolysiloxanes are well known as antifoams, but the fluid organopolysiloxanes commonly used as antifoams generally have a surface tension below 27 mN/m. Polydimethylsiloxane, for example, has a surface tension of 21 mN/m.

The invention includes the use of a composition comprising (a) a hydrophobic fluid organopolysiloxane having a surface tension of at least 27 mN/m and less than 40 mN/m, and (b) a finely divided solid hydrophobic filler dispersed in the hydrophobic fluid, to inhibit foam in the rinsing step of a washing process. In particular, such a composition is used to inhibit foam in the rinsing step by incorporating the composition in the washing process, for example by adding it to the detergent composition used for washing.

A composition according to another aspect of the present concepts for inhibiting foam in the rinsing step of a washing process without substantially reducing foam in the washing step of the washing process comprises (a) a fluid organopolysiloxane containing pendant esterified carboxyalkyl groups, and (b) a finely divided solid hydrophobic filler dispersed in the fluid organopolysiloxane.

A composition according to another aspect of the present concepts for inhibiting foam in the rinsing step of a washing process without substantially reducing foam in the washing step of the washing process comprises (a) a fluid organopolysiloxane and (b) a finely divided solid hydrophobic filler dispersed in the fluid organopolysiloxane, wherein the fluid organopolysiloxane (a) is a trimethylsiloxy-terminated poly (phenylmethylsiloxane).

One type of fluid organopolysiloxane which has a surface tension of at least 27 mN/m and which is suitable for use in embodiments of the present invention is a fluid organopolysiloxane containing pendant esterified carboxyalkyl groups. The fluid organopolysiloxane containing pendant esterified carboxyalkyl groups can, for example, be a substantially linear polydiorganosiloxane or can be a branched organopolysiloxane containing for example up to 10 mole % branching units. The carboxalkyl groups can, for example, contain 2 to 12 carbon atoms, particularly 2 to 5 carbon atoms, and can, for example, be carboxymethyl, 2-carboxyethyl, 2-methyl-2-carboxyethyl or 2-ethyl-2-carboxyethyl groups. The carboxyalkyl groups can be esterified by alkyl, aryl, aralkyl or cycloalkyl groups, for example the carboxyalkyl groups can each be esterified by an alkyl group having 1 to 20 carbon atoms. Preferably, all or most of the carboxyalkyl groups are esterified by an alkyl group having 8 to 18 carbon atoms, for example a n-octyl, 2-ethylhexyl, lauryl, tetradecyl, hexadecyl or stearyl group. A mixture of different alkyl groups, for example alkyl groups of different chain length, can be used such as a mixture of $C_{12}$ and $C_{14}$ alkyl groups.

Preferably, at least 10% of the siloxane units in such an organopolysiloxane carry a pendant esterified carboxyalkyl group, for example 25 to 100% of the siloxane units may carry a pendant esterified carboxyalkyl group. Other substituents in the organopolysiloxane can, for example, be selected from alkyl groups having 1 to 20 carbon atoms and phenyl groups. The organopolysiloxane can be prepared by reaction of an organopolysiloxane containing Si—H groups with an ester of an ethylenically unsaturated carboxylic acid, for example an acrylate or methacrylate, in the presence of a hydrosilylation catalyst. The organopolysiloxane containing Si—H groups can, for example, be poly(methylhydrogensiloxane) or a dimethylsiloxane methylhydrogensiloxane copolymer, so that in many cases most or all of the siloxane groups in the organopolysiloxane contain a methyl substituent.

It may be preferred that the fluid organopolysiloxane containing pendant esterified carboxyalkyl groups also has pendant alkyl substituents having 2 to 20 carbon atoms in addition to esterified carboxyalkyl groups and methyl groups. Such alkyl substituents can, for example, be ethyl, hexyl, octyl, lauryl, tetradecyl, hexadecyl or stearyl substituents. In particular, it may be preferred that the fluid organopolysiloxane contains alkyl substituents having 8 to 18 carbon atoms bonded to Si atoms of the organopolysiloxane as well as methyl groups and carboxyalkyl groups esterified by an alkyl group having 8 to 18 carbon atoms. The fluid organopolysiloxane can, for example, be prepared by reacting poly(methylhydrogensiloxane) or a dimethylsiloxane methylhydrogensiloxane copolymer with a mixture of one or more alpha-alkene having 8 to 18 carbon atoms and one or more 8-18C alkyl methacrylate or acrylate ester, such as a mixture of $C_{12}$ to $C_{14}$ alkenes and $C_{12}$ to $C_{14}$ alkyl methacrylates. The molar ratio of pendant esterified carboxyalkyl groups to pendant alkyl substituents having 2 to 20 carbon atoms can, for example, be in the range 10:1 to 1:2, with each siloxane unit generally containing a methyl group. A substantially linear polydiorganosiloxane comprising methyl $C_{12-14}$ alkyl siloxane units and methyl 2-methyl-2-carboxyethyl siloxane units in substantially equimolar amounts, in which the carboxyethyl groups are esterified by $C_{12-14}$ alkyl groups has a surface tension of 27.2 mN/m.

An alternative type of fluid organopolysiloxane which has a surface tension of at least 27 mN/m and is suitable for use in embodiments of the present invention is a fluid organopolysiloxane containing aryl groups, preferably phenyl groups, bonded to silicon. The aryl organopolysiloxane can, for example, be a substantially linear polydiorganosiloxane or can be a branched organopolysiloxane containing for example up to 10 mole % branching units. Organopolysiloxanes having a phenyl group bonded to substantially all the silicon atoms of the organopolysiloxane are particularly effective. One preferred example of such an organopolysiloxane is a poly(methylphenylsiloxane). One trimethylsiloxy-terminated poly(methylphenylsiloxane), known as a heat transfer fluid, has a surface tension of 27.1 mN/m. A silanol-terminated poly(methylphenylsiloxane) of similar molecular weight has a surface tension of 33.9 mN/m. Another poly(methylphenylsiloxane), described in Example 1 of WO-2008/152042, has a surface tension of 32.8 mN/m. All of these fluid organopolysiloxanes containing phenyl groups are suitable for use in embodiments of the present invention as hydrophobic fluid of the antifoam.

The hydrophobic fluid (a) used as an antifoam in embodiments of the present invention can alternatively be an organic fluid containing no silicon. It can, for example, be a hydrocarbon fluid such as a liquid polyisobutylene. The liquid polyisobutylene sold by Univar (The Netherlands) under the trade mark Dynapak poly 55 has a surface tension of 30.4 mN/m.

Alternative organic hydrophobic fluids which is suitable for use as the hydrophobic fluid (a) in the antifoam in the embodiments of the present invention are polyethers in which the repeating ether unit has at least 3 carbon atoms, for example polypropylene oxide, polybutylene oxide or polytetramethylene oxide. Polypropylene oxide has a surface tension of 29.0 mN/m.

The foam control composition contains a hydrophobic filler (b) dispersed in the polydiorganosiloxane fluid. Hydrophobic fillers for foam control agents are well known and are particulate materials which are solid at 100° C., such as silica, preferably with a surface area as measured by BET measurement of at least 50 $m^2$/g., titania, ground quartz, alumina, an aluminosilicate, zinc oxide, magnesium oxide, a salt of an aliphatic carboxylic acids, a reaction product of an isocyanate with an amine, e.g. cyclohexylamine, or an alkyl amide such as ethylenebisstearamide or methylenebisstearamide. Mixtures of two or more of these can be used.

Some of the fillers mentioned above are not hydrophobic in nature, but can be used if made hydrophobic. This can be done either in situ (i.e. when dispersed in the polysiloxane fluid), or by pre-treatment of the filler prior to mixing with the polysiloxane fluid. A preferred filler is silica which is made hydrophobic. Preferred silica materials are those which are prepared by heating, e.g. fumed silica, or precipitation. The silica filler may, for example, have an average particle size of 0.5 to 50 μm, preferably 2 to 30 and most preferably 5 to 25 μm. It can be made hydrophobic by treatment with a fatty acid, but is preferably made hydrophobic by the use of methyl substituted organosilicon materials such as dimethylsiloxane polymers which are end-blocked with silanol or silicon-bonded alkoxy groups, hexamethyldisilazane, hexamethyldisiloxane or organosilicon resins containing $(CH_3)_3SiO_{1/2}$ groups and silanol groups. Hydrophobing is generally carried out at a temperature of at least 100° C. Mixtures of fillers can be used, for example a highly hydrophobic silica filler such as that sold under the trademark Sipernat® D10 from Evonik Industries (Germany) can be used together with a partially hydrophobic silica such as that sold under the trademark Aerosil® R972 from Evonik Industries.

The amount of hydrophobic filler (b) in the foam control composition of embodiments of the invention is preferably 0.5-50% by weight based on the hydrophobic fluid (a), more preferably from 1 up to 10 or 15% and most preferably 2 to 8% by weight.

The detergent composition of embodiments of the invention is preferably a laundry detergent, but can alternatively be a detergent for dish washing or a detergent composition for personal care use such as a shampoo, shower gel or soap bar. In all of these applications, the consumer may prefer to see lather during the washing step but rapid defoaming in the rinsing step.

The detergent composition comprises at least one detersive surfactant, which may be chosen from soap and non-soap anionic, cationic, nonionic, amphoteric and zwitterionic detergent-active surfactants, and mixtures thereof. Many suitable detergent-active surfactants are available and are fully described in the literature, for example, in "Surface-Active Agents and Detergents", Volumes I and II, by Schwartz, Perry and Berch. The preferred detersive surfactants that can be used are soaps and/or synthetic non-soap anionic and/or nonionic compounds. The total amount of surfactant present is suitably within the range of from 5 to 40 wt % of the detergent composition.

Examples of anionic surfactants include alkylbenzene sulphonates, particularly linear alkylbenzene sulphonates having an alkyl chain length of 8 to 16 carbon atoms; primary and secondary alkyl sulphates, particularly primary alkyl sulphates having an alkyl chain length of 8 to 16 carbon atoms; alkyl ethersulphates; olefin sulphonates; alkyl xylene sulphonates; dialkyl sulphosuccinates; and fatty acid ester sulphonates. Sodium salts are generally preferred. The detergent composition preferably contains an anionic surfactant, optionally with a nonionic surfactant.

Nonionic surfactants that may be used include the primary and secondary alcohol ethoxylates, especially aliphatic alcohols having 8 to 20 carbon atoms ethoxylated with an average of from 1 to 20 moles, preferably 1 to 10 moles, of ethylene oxide per mole of alcohol. Suitable non-ethoxylated nonionic surfactants include alkylpolyglycosides, glycerol monoethers, and polyhydroxyamides.

Examples of cationic organic detergent surfactants include alkylamine salts, quaternary ammonium salts, sulphonium salts and phosphonium salts.

The detergent compositions of embodiments of the invention will usually also contain one or more detergency builders. The total amount of detergency builder in the compositions will suitably range from 5 to 80 wt %, preferably from 10 to 60 wt %. Inorganic builders that may be present include sodium carbonate, crystalline and amorphous aluminosilicates, for example, zeolites, and layered silicates. Inorganic phosphate builders, for example, sodium orthophosphate, pyrophosphate and tripolyphosphate, may also be present. Organic builders that may be present include polycarboxylate polymers such as polyacrylates, acrylic/maleic copolymers, and acrylic phosphinates; monomeric polycarboxylates such as citrates, gluconates, oxydisuccinates, glycerol mono-, di- and trisuccinates, carboxymethyloxysuccinates, carboxymethyloxymalonates, dipicolinates, hydroxyethyliminodiacetates, alkyl- and alkenylmalonates and succinates; and sulphonated fatty acid salts. Builders, both inorganic and organic, are preferably present in alkali metal salt, especially sodium salt, form.

The detergent composition of embodiments of the invention may also suitably contain a peroxy bleach compound, for example, an inorganic persalt or an organic peroxyacid, capable of yielding hydrogen peroxide in aqueous solution. Preferred inorganic persalts are sodium perborate monohydrate and tetrahydrate, and sodium percarbonate. The peroxy bleach compound may be used in conjunction with a bleach activator (bleach precursor), for example a peroxycarboxylic acid precursor, more especially a peracetic acid precursor such as tetraacetyl ethylenediamine, or a peroxybenzoic acid or peroxycarbonic acid precursor.

Detergent compositions intended for personal care use such as shampoo compositions can contain other ingredients selected for example from conditioners to facilitate combing and/or styling of the hair and/or to improve the shine and/or softness of the hair, perfumes, fragrances, colorants such as dyes, essential oils, vitamins, buffering agents, stabilizers and preservatives.

The detergent composition of embodiments of the invention may be in powder, liquid or tablet form, or in the form of a solid bar (soap bar). Laundry detergents for hand washing or for use in semi-automatic machines are commonly sold in powder form. Detergent powders can, for example, be prepared by spray-drying a slurry of compatible heat insensitive ingredients, or by mixing and granulation of raw materials, preferably using a high-speed mixer/granulator. Less robust or more heat sensitive ingredients can be subsequently incorporated into the detergent powder; the foam-inhibiting composition of the invention is preferably subsequently incorporated in this way.

Examples of commercial detergents in which the foam inhibiting composition of the invention can be incorporated include Omo Total as sold by Unilever in China; Omo MA as sold by Unilever in Brazil; Persil® Express as sold by Henkel in Greece; and Ariel® as sold by The Procter & Gamble Company in China.

For use in a detergent composition sold in powder form, the foam inhibiting composition of the invention may be in granule form. The foam inhibiting composition of the invention can, for example, be supported on a particulate carrier which is agglomerated into granules by a binder.

Examples of carriers are sodium sulfate, zeolites, other aluminosilicates or silicates, for example magnesium silicate, phosphates, for example sodium tripolyphosphate, sodium carbonate, sodium perborate, a cellulose derivative such as sodium carboxymethylcellulose, granulated starch, clay, sodium citrate, sodium acetate, sodium sesquicarbonate, sodium bicarbonate and native starch. The mean particle size of the carrier is preferably in the range 1 to 250 µm, particularly from 5 µm up to 30 or 40 µm. The carrier particles generally form from 60% by weight to 85 or 90% by weight of the granulated product. The foam inhibiting hydrophobic fluid generally forms from 5% by weight to 20 or 25% by weight of the granulated product.

The binder is a material which can be applied to the carrier as a liquid binding medium and which can be solidified to a solid which binds carrier particles together. The binder is preferably a material which at room temperature, i.e. from 20 to 25° C., has a solid consistency, for example a waxy material of melting point 35 to 100° C. Such a binder can be applied in a molten state to the sodium sulfate carrier and can be solidified by cooling to agglomerate the carrier. Alternatively, the binder can comprise a water-soluble or water-dispersible polymer, preferably a film-forming polymer, which can be applied as an aqueous solution or emulsion to the carrier and can be solidified by drying to agglomerate the carrier. The binder may, for example, be present in the foam inhibiting granules at 10-200% by weight based on the hydrophobic foam inhibiting fluid, most preferably at 20 up to 100 or 120% based on the foam inhibiting fluid.

The foam inhibiting granules can be made by an agglomeration process in which the antifoam, comprising hydrophobic fluid (a) with a finely divided solid hydrophobic filler (b) dispersed therein, and the liquid binding medium are sprayed onto the carrier particles while agitating the particles. The particles can, for example, be agitated in a high shear mixer through which the particles pass continuously. One type of suitable mixer is a vertical, continuous high shear mixer in which the foam inhibiting fluid and the binder in a liquid state are sprayed onto the particles. One example of such a mixer is a Flexomix mixer supplied by Hosokawa Schugi. Alternative suitable mixers include horizontal high shear mixers, in which an annular layer of the powder—liquid mixture is formed in the mixing chamber, with a residence time of a few seconds up to about 2 minutes. Examples of this family of machines are pin mixers (e.g. TAG series supplied by LB, RM-type machines from Rubberg-Mischtechnik or pin mixers supplied by Lodige), and paddle mixers. Other suitable mixers include Glatt granulators, ploughshare mixers, as sold for example by Lodige GmbH, twin counter-rotating paddle mixers, known as Forberg-type mixers, and intensive mixers including a high shear mixing arm within a rotating cylindrical vessel.

Foam inhibiting granules generally have a mean particle diameter of at least 0.1 mm, preferably over 0.25 or 0.5 mm, up to a mean diameter of 1.2 or 1.5 or even 2 mm. Granules according to the invention of this particle size, particularly 0.5 to 1 mm, have good flow properties and resistance to compaction.

For use in shampoo, laundry liquid detergent or liquid dishwashing detergent the foam control agent may be in an emulsion form, preferably an oil-in-water emulsion. The emulsions may be macro-emulsions or micro-emulsions. In general, they comprise the foam control agent as the disperse phase, one or more surfactants, water and standard additives, such as preservatives, viscosity modifiers and thickeners. The surfactants may be selected from anionic, cationic, nonionic or amphoteric materials as described above. The concentration of the foam control agent in the emulsion can, for example, be 10 to 50%, more preferably 25 to 40%.

The hydrophobic foam inhibiting fluid (a) is generally present in the detergent composition at 0.01 to 2% by weight, preferably 0.03 to 0.2% by weight of the detergent composition. A granulated foam control composition according to the invention is typically added to detergent powders at 0.1 to 10% by weight, preferably 0.2 to 0.5 or 1.0%.

EXAMPLES

These examples are intended to illustrate the invention to one of ordinary skill in the art and should not be interpreted as limiting the scope of the invention set forth in the claims. All parts and percentages in the examples are on a weight basis and all measurements were indicated at about 25° C., unless indicated to the contrary.

Example 1

A fluid substantially linear polydiorganosiloxane comprising methyl $C_{12-14}$ alkyl siloxane units and methyl 2-methyl-2-carboxyethyl siloxane units in substantially equimolar amounts, in which the carboxyethyl groups are esterified by $C_{12-13}$ alkyl groups, was compounded with 6% Sipernat® D10 hydrophobic silica to form a foam inhibiting composition.

The foam control properties of the composition were tested in a series of shake tests. In these tests 0.35 g OMO Total detergent powder as sold by Unilever in China was dissolved in 100 g demineralised water in a 250 ml bottle. 4.5 mg of antifoam composition was absorbed onto 1 g sucrose and was added to the solution. This procedure was used to avoid errors arising from the viscous antifoam fluid adhering to the walls of vessels used to transfer it. A scale from 0 to 100% was marked on the bottle: 0 is the interface between liquid and air and 100% is the top of the bottle. The bottle was capped without mixing or agitation and placed in the clamp on the shaker arm of a shaking machine whose shake speed was fixed at 400 strokes/minute. The bottle was shaken during exactly 8 seconds, then shaking was stopped and the initial foam height after shaking and the foam height after 2 minutes (120 seconds) collapse time were recorded. The shake test was repeated using different times of shaking (32, 48 and 96 seconds). The results are recorded in Table 1; the initial foam height is listed as 'init' and the foam height after 2 minutes is listed as '2 m'.

The 3.5 g/L solution of detergent powder used in this first set of tests simulated the washing step of a wash cycle. In a second set of tests the detergent solution was diluted to 0.47 g/L (thereby also diluting the antifoam concentration), to simulate the first rinse step of a wash cycle. In a third set of tests, the detergent solution was further diluted to 0.062 g/L, to simulate the second rinse step.

In a comparative example C1, the shake tests were carried out using the same amounts of OMO Total detergent powder and sugar without added antifoam. These results are also shown in Table 1.

Example 2

Example 1 was repeated using Dynapak poly 55 liquid polyisobutylene in place of the fluid polydiorganosiloxane. The results of the shake tests carried out in Example 2 are shown in Table 1.

Example 3

Example 1 was repeated using trimethylsiloxy-terminated poly(methylphenylsiloxane) in place of the fluid polydiorganosiloxane. In Example 3, the poly(methylphenylsiloxane) fluid was compounded with 4% SipernatO D10 hydrophobic silica to form the foam inhibiting composition. The results of the shake tests carried out in Example 3 are shown in Table 1.

In a comparative example C2, Example 1 was repeated using trimethylsiloxy-terminated polydimethylsiloxane in place of the fluid polydiorganosiloxane. The results of the shake tests carried out in comparative example C2 are shown in Table 1.

TABLE 1

| | | Foam Height (%) | | | |
|---|---|---|---|---|---|
| Detergent concentration and time of shaking | Without antifoam (C1) | Sample 1 | Sample 2 | Sample 3 | Comparative Sample C2 |
| 3.5 g/L, 8 s, init | 70 | 60 | 60 | 60 | 20 |
| 3.5 g/L, 8 s, 2 m | 70 | 55 | 60 | 60 | 20 |
| 3.5 g/L, 32 s, init | 100 | 90 | 100 | 100 | 35 |
| 3.5 g/L, 32 s, 2 m | 100 | 80 | 100 | 100 | 30 |
| 3.5 g/L, 48 s, init | 100 | 100 | 100 | 100 | 40 |
| 3.5 g/L, 48 s, 2 m | 100 | 100 | 100 | 100 | 40 |
| 3.5 g/L, 96 s, init | 100 | 100 | 100 | 100 | 45 |
| 3.5 g/L, 96 s, 2 m | 100 | 100 | 100 | 100 | 45 |
| 0.47 g/L, 8 s, init | 13 | 15 | 15 | 10 | 0 |
| 0.47 g/L, 8 s, 2 m | 13 | 15 | 15 | 10 | 0 |
| 0.47 g/L, 32 s, init | 15 | 15 | 15 | 10 | 1 |
| 0.47 g/L, 32 s, 2 m | 15 | 10 | 15 | 10 | 1 |
| 0.47 g/L, 48 s, init | 19 | 18 | 15 | 18 | 5 |
| 0.47 g/L, 48 s, 2 m | 18 | 15 | 15 | 18 | 5 |
| 0.47 g/L, 96 s, init | 20 | 20 | 15 | 20 | 10 |
| 0.47 g/L, 96 s, 2 m | 20 | 18 | 15 | 20 | 10 |
| 0.062 g/L, 8 s, init | 5 | 0 | 0 | 0 | 0 |
| 0.062 g/L, 8 s, 2 m | 5 | 0 | 0 | 0 | 0 |
| 0.062 g/L, 32 s, init | 8 | 0 | 0 | 0 | 0 |
| 0.062 g/L, 32 s, 2 m | 7 | 0 | 0 | 0 | 0 |
| 0.062 g/L, 48 s, init | 10 | 0 | 0 | 0 | 0 |
| 0.062 g/L, 48 s, 2 m | 10 | 0 | 0 | 0 | 0 |
| 0.062 g/L, 96 s, init | 10 | 0 | 0 | 0 | 0 |
| 0.062 g/L, 96 s, 2 m | 10 | 0 | 0 | 0 | 0 |

It can be seen from Table 1 that the antifoam compositions of the invention of Examples 1 to 3 had very little effect on the foam generated at a detergent concentration equal to that in the washing step, but substantially reduced the foam when the detergent solution was diluted to concentrations equal to those in the rinse steps, despite the concentration of antifoam being correspondingly diluted. No lasting foam was seen at a detergent concentration equal to that in the second rinse step. A consumer would be satisfied that rinsing was complete. In comparative example C1 without the antifoam composition of the invention, a noticeable amount of foam was seen at a detergent concentration equal to that in the second rinse step. In comparative example C2 using a conventional antifoam, the foam level in the wash was substantially reduced to the extent that a consumer might doubt the detergent efficiency.

The antifoam composition of Example 1 was tested in a laundry hand washing process. 5.25 g OMO Total detergent powder as sold in China mixed with 4 mg of the antifoam composition was added to 1.5 L water of hardness 24 FH, Ca/Mg 4:1 at a temperature of 30° C. After the powder was completely dissolved, the wash solution was whisked for 20 seconds and 300 g woven cotton pillow cases were added. The wash was soaked for 30 minutes then each pillow case was dipped in the wash liquor 3 times and squeezed. After the third squeeze the fabric load was removed from the wash with a carry over of 400 g liquid (weight of wet fabric 700 g). The foam height in the wash liquor was measured with a ruler.

The squeezed wet fabric load was added to 2.6 L rinse water of the same hardness. Each pillow case was dipped in the rinse liquor 3 times and squeezed. After the third squeeze the fabric load was removed from the rinse with a carry over of 400 g liquid (weight of wet fabric 700 g).

The squeezed wet fabric load after rinsing was added to 2.6 L rinse water of the same hardness for a second rinse step using the same rinsing procedure. After removal of the fabric load with a carry over of 400 g liquid (weight of wet fabric 700 g) the foam height in the second rinse liquor was measured. After removal of the fabric, a picture was taken from the top of the rinse vessel and the image was analyzed with a software that facilitates counting the number of pixels darker than a defined threshold which correspond to the areas where no foam is present anymore at the surface. The higher the number of pixels, the more efficient is the rinse in removing foam. From the number of pixels, the % of the foam surface covered by foam can be calculated.

In a comparative experiment, the hand washing tests were repeated using 5.25 g OMO Total detergent powder to which no antifoam had been added. The results of the hand wash and rinse tests are shown in Table 2. The results for foam after rinse are those using the picture analysis method (number of pixels after the second rinse) were

TABLE 2

| Sample | Foam height after wash | Rinse foam (pixels) | Surface free of foam after rinse |
|---|---|---|---|
| 4 | 3.7 cm | 920338 | 30% |
| Comparative | 3.8 cm | 1278 | 0.1% |

As can be seen from Table 2, the antifoam composition of Sample 4 had no significant effect on foam during washing, but substantially removed the foam that was otherwise present after rinsing.

Example 4

A fluid substantially linear polydiorganosiloxane comprising methyl $C_{12-14}$ alkyl siloxane units and methyl 2-methyl-2-carboxyethyl siloxane units in substantially equimolar amounts, in which the carboxyethyl groups are esterified by $C_{12-13}$ alkyl groups, was compounded with 6% CAB-O-SIL® TS-530 from Cabot Corporation (Boston, Mass.) and 3% AEROSIL® R 972.

The resulting compound was emulsified with fatty alcohol ethoxylates, Volpo S2 and Volpo S20 from Croda (Europe). 0.98 g of Volpo S2 and 0.98 g of Volpo S20 were added to 10 g of the compound which had been pre-heated at a temperature of 70° C. The ingredients were mixed in a dental mixer for 30 seconds. 15.7 g of an aqueous solution of Ketrol RD (8%) from CP Kelco (Europe), Natrosol® LR (23%) from Ashland (Europe) and Kathon® LX (1%) from The Dow Chemical Company (Midland, Mich.) are then added, followed by the addition of 22.5 g of demineralized water.

The resulting emulsion was evaluated in a shampoo formulation. 10 μL of the emulsion was mixed slowly with a shampoo (Pantene® from The Procter and Gamble Company). The resulting mixture was diluted into 1 L of water. The foam control properties of the composition were tested in a series of shake tests as described in Example 1. In the present example, only the initial foam height was recorded after 8, 32, 48 or 96 seconds shaking The results are recorded in Table 3.

The concentration of shampoo in demineralized water was first defined as 6 g/L, to simulate the washing step of a hair cleaning operation. The concentration of shampoo used in a second set of tests was 1 g/L, to simulate the rinse step.

In a comparative experiment, the shake tests were carried out using the same concentrations of shampoo without added antifoam. These results are also shown in Table 3.

Example 5

Example 4 was repeated using Dynapak poly 55 liquid polyisobutylene in place of the fluid polydiorganosiloxane. The results of the shake tests carried out in Example 4 are shown in Table 3.

TABLE 3

| Shampoo | Foam Height (%) | | |
|---|---|---|---|
| concentration and time of shaking | Without antifoam (Comparison) | Sample 5 | Sample 6 |
| 6 g/L, 8 s | 100 | 50 | 70 |
| 6 g/L, 32 s | 100 | 90 | 100 |
| 6 g/L, 48 s | 100 | 100 | 100 |
| 6 g/L, 96 s | 100 | 100 | 100 |
| 1 g/L, 8 s | 60 | 20 | 40 |
| 1 g/L, 32 s | 100 | 40 | 50 |
| 1 g/L, 48 s | 100 | 50 | 50 |
| 1 g/L, 96 s | 100 | 60 | 70 |

It can be seen from Table 3 that the antifoam compositions of the invention of Samples 5 and 6 had very little effect on the foam generated at a shampoo concentration equal to that in the washing step, but substantially reduced the foam at detergent concentrations equal to those in the rinse steps.

While the invention is susceptible to various modifications and alternative forms, specific embodiments have been shown by way of example in the examples and described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention claimed is:

1. A process for washing a substrate comprising:
   (a) providing a detergent composition including a surfactant and an antifoam,
       wherein the antifoam comprises
           (A) a hydrophobic fluid having a surface tension of at least 27 mN/m and less than 40 mN/m, and
           (B) a finely divided solid hydrophobic filler dispersed in the (A) hydrophobic fluid,
       wherein the surfactant has a critical micelle concentration of between 0.2 g/L and 0.6 g/L,
       wherein the detergent composition is in powder, liquid or tablet form, or in the form of a solid bar, and
       wherein the detergent composition is free of an organosilicon resin;
   (b) washing the substrate in an aqueous medium with the detergent composition,
       whereby the detergent composition is applied to the substrate during the (b) washing step; and
   (c) rinsing the substrate with the applied detergent composition with water,
       whereby foaming of the detergent composition during the (c) rinsing step is inhibited by the antifoam; and
       wherein each of the (b) washing and (c) rinsing steps occurs by hand; and
       wherein the concentration of the surfactant in the aqueous medium during the (b) washing step is above the critical micelle concentration and the concentration of the surfactant in the rinse water in the (c) rinsing step is below the critical micelle concentration.

2. A process for washing a substrate according to claim 1 wherein the surfactant comprises an anionic surfactant.

3. A process for washing a substrate according to claim 1 wherein the (B) finely divided solid hydrophobic filler is hydrophobic silica.

4. A process for washing a substrate according to claim 1 wherein the detergent composition is a detergent composition for dish washing.

5. A process for washing a substrate according to claim 1 wherein the detergent composition is in tablet form, or in the form of a solid bar.

6. A process for washing a substrate according to claim 1 wherein the surfactant is present in an amount of from 5 to 40 wt % of the detergent composition.

7. A process for washing a substrate according to claim 1 wherein during the (b) washing step, the substrate is dipped in the aqueous medium with the detergent composition and squeezed by hand, and during the (c) rinsing step, the substrate with the applied detergent composition is dipped in the water and squeezed by hand.

8. A process for washing a substrate according to claim 1 wherein the substrate comprises fabric and the detergent composition is a laundry detergent composition.

9. A process for washing a substrate according to claim 8 wherein the laundry detergent composition is in powder form and contains a granulated foam control agent comprising the antifoam supported on a particulate carrier.

10. A process for washing a substrate according to claim 1 wherein the (A) hydrophobic fluid is polyisobutylene.

11. A process for washing a substrate according to claim 10 wherein the (B) finely divided solid hydrophobic filler is hydrophobic silica.

12. A process for washing a substrate according to claim 1 wherein the detergent composition is a detergent composition for personal care.

13. A process for washing a substrate according to claim 12 wherein the detergent composition for personal care is a shampoo, shower gel or soap bar.

14. A process for washing a substrate according to claim 1 wherein the (A) hydrophobic fluid is an organopolysiloxane fluid.

15. A process for washing a substrate according to claim 14 wherein the (B) finely divided solid hydrophobic filler is hydrophobic silica.

16. A process for washing a substrate according to claim 14 wherein the organopolysiloxane fluid contains carboxyalkyl groups esterified by an alkyl group having 8 to 18 carbon atoms.

17. A process for washing a substrate according to claim 16 wherein the organopolysiloxane fluid also contains alkyl substituents having 8 to 18 carbon atoms bonded to silicon atoms of the organopolysiloxane.

18. A process for washing a substrate according to claim 14 wherein the organopolysiloxane fluid contains silicon-bonded phenyl groups.

19. A process for washing a substrate according to claim 18 wherein the organopolysiloxane fluid comprises a trimethylsiloxy-terminated poly(methylphenylsiloxane).

20. A process for washing a substrate according to claim 19 wherein the (B) finely divided solid hydrophobic filler is hydrophobic silica.

* * * * *